(12) United States Patent
Bucala et al.

(10) Patent No.: US 6,413,939 B1
(45) Date of Patent: Jul. 2, 2002

(54) INDUCIBLE PHOSPHOFRUCTOKINASE AND THE WARBURG EFFECT

(75) Inventors: Richard J. Bucala, Cos Cob, CT (US); Jason Chesney, New York; Robert A. Mitchell, Great Neck, both of NY (US)

(73) Assignee: The Picower Institute for Medical Research, Manhasset, NY (US)

( * ) Notice: Subject to any disclaimer, the term of this patent is extended or adjusted under 35 U.S.C. 154(b) by 0 days.

(21) Appl. No.: 08/961,578

(22) Filed: Oct. 31, 1997

(51) Int. Cl.$^7$ .................... A61K 48/00; A61K 39/395; C12Q 1/68; C07H 21/04
(52) U.S. Cl. ................... 514/44; 424/130.1; 435/6; 514/44; 530/387.1; 536/23.1; 536/24.5
(58) Field of Search ............................... 536/23.1, 24.5; 514/44; 435/6; 424/130.1; 530/387.1

(56) References Cited

U.S. PATENT DOCUMENTS 6,255,046 B1   7/2001   Bucala et al. .................. 435/4

OTHER PUBLICATIONS

Rojanasakul, Antisense oligonucleotide therapeutics: drug delivery and targeting, Advanced Drug Delivery Reviews, vol. 18, pp. 115–131, 1996.*
Gewirtz et al., Facilitating oligonucleotide delivery: Helping antisense deliver on its promise, Proc. Natl. Acad. Sci., vol. 93, pp. 3161–3163, Apr. 1996.*
Branch, A good antisense is hard to find, TIBS, vol. 23, pp. 45–50, Feb. 1998.*
Stein, Hybridization prediction gets to first base, Nature Biotechnology, vol. 17, pp. 751–752, Aug. 1999.*
Argilés, J.M. and Azcón–Bieto, J., The metabolic environment of cancer, *Molecular and Cellular Biochemistry* 81:3–17, 1988.
Sakai, A. et al., Cloning of cDNA Encoding for a Novel Isozyme of Fructose 6–Phosphate,2–Kinase/Fructose 2,6–Bisphosphatase from Human Placenta, *J. Biochem.* 119, 506–511, 1996.
Watanabe, F. et al., Novel Isoforms of Rat Brain Fructose 6–Phosphate 2–Kinase/Fructose 2,6–Bisphaphatase Are Generated by Tissue–Specific Alternative Splicing, *Journal of Neurochemistry* 69(1), 1997.
Hamilton et al., Identification of PRG1, A Novel Progestin–Responsive Gene with Sequence Homology to 6–Phosphofructo–2–Kinase/Fructose–2,6–Bisphosphatase, *Mol. Endocrinology* 11:490–502, 1997.
Textbook Section entitled Phosphofructokinase is the Key Enzyme in the Control of Glycolysis, *Metabolic Energy*, Part III, Chapter 19, p. 493–494.
Greenberg, et al., "Control of the Decay of Labile Protooncogene and Cytokine mRNAs", Control of Messenger RNA Stability, Belasco, et al. (eds.), Academic Press, Inc., New York (1993).

Caput, et al., "Identification of a Common Nucleotide Sequence in the 3'–Untranslated Region of mRNA Molecules Specifying Inflammatory Mediators", Proc. Natl. Acad. Sci. USA, 83, 1670–1674 (1986).
Shaw, et al., "A Conserved AU Sequence from 3' Untranslated Region of GM–CSF mRNA Mediates Selective mRNA Degradation", Cell, 46, 659–667 (1986).
Lange, et al., "Sequence of Human Liver 6–Phosphofructo–2–Kinase/Fructose–2,6–Bisphophatase", Nucleic Acids Research, 18:12, 3652 (1990).
Lee, et al., "Activation of the Transforming Potential of the Human fos Proto–Oncogene Requires Message Stabilization and Results in Increased Amounts of Partially Modified fos Protein", Molecular and Cellular Biology, 8:12, 5521–5527 (1988).
Rabbitts, et al., "Truncation of Exon 1 from the c–myc Gene Results in Prolonged c–myc mRNA Stability", EMBO J., 4, 3727–3733 (1985).
Piechaczyk, et al., "Posttranscriptional Mechanisms are Responsible for Accumulation of Truncated c–myc RNAs in Murine Plasma Cell Tumors", Cell, 42, 589–597 (1985).
Eigenbrodt, et al., "Glycolysis—One of the Keys to Cancer?", Trends Pharmacol. Sci., 1, 240–245 (1980). cited in specification as "Eifenbrody, pp. 24–245".
Van Schaftingen, et al., "A Kinetic Study of Pyrophosphate: Fructose–6–Phosphate Phosphotransferase from Potato Tubers", Eur. J. Biochen., 129, 191–195 (1982).
Van Schaftingten, et al., "D–Fructose 2,6–Bisphosphate", Chapter 2.25, Methods Enz. Anal., 6, 335–341 (1984).
Sant, et al., "Antifolates Induce Inhibition of Amido Phosphoribosyltransferase in Leukemia Cells", Journal of Biological Chemistry, 267:16, 11038–11045 (1992). cited as "vol. 16" in specification.
Taetle, et al., "Use of Nude Mouse Xenografts as Preclinical Drug Screens: In Vivo of Established Chemotherapeutic Agents Against Melanoma and Ovarian Carcinoma Xenografts", Cancer Treatment Reports, 71:3, 297–304 (1987).
Shimamoto, et al., "Antitumor Effects of a Novel Phenoxazine Derivative on Human Leukemia Cell Lines in vitro and in vivo", Clin. Cancer Res., 7:3, 704–708 (Abstract).

* cited by examiner

Primary Examiner—Andrew Wang
(74) Attorney, Agent, or Firm—Piper Rudnick LLP; Steven B. Kelber

(57) ABSTRACT

There is disclosed a cancer malignancy diagnostic assay comprising obtaining a sample of a body fluid or tissue, performing a sequence identity assay to look for the presence of PFK-2 specific sequences; an anticancer pharmaceutical composition comprising a specific antisense oligonucleotide to the inventive isolated PFK-2 sequence and a pharmaceutically acceptable oligonucleotide carrier; and a method for finding therapeutically active anti-cancer compounds comprising screening compounds for activity to inhibit PFK-2 but not PFK.

10 Claims, 14 Drawing Sheets

| | | |
|---|---|---|
| iPFK-2 | M-P-L-ELTQSRVQKIWPVDH-R-PS-L-PRSCG---PKLTNSPTVIVMWGLPARGKTYISKKLTRYLMIGVPYKVFNVGEYRREAVKQYSSYNFF-RPDN-EEAMKV | 98 |
| Liver PFK-2 | MSPEMGELTQTRLQKIWIP--HSSGSSRLQRRR-GSSIPQFTNSPTMVIMWGLPARGKTYISTKLTRYLMIGTPTKVFNLGQYRREAVS-YKNYEFF-LPDNME-ALQI | 104 |
| iPFK-2 | RKQCALAALRDVKSYLAKEGGQIAVFDATNTTRERRHMILHFGKENDFKAFFIESVCDDPTVVASNIMEVKISSPDY-KDCNSAE-AMDDFMKRISCYEASYQPLDPDK- | 205 |
| Liver PFK-2 | RKQCALAALKDVHNYLSHEEGHVAVFDATNTTRERRSLILQFAKEHGYKVFFIESICNDPGIIAENIRQVKLGSPDY-IDCDR-EKVLEDFLKRIECYEVNYQPLD-EE- | 210 |
| iPFK-2 | CDRDLSLIKVIDVGRRFLVNRVQDHIQSRIVYYLMNIHVQPRTIYLCRHGENE-HNLQGRIGGDSGLSSRGKKFA-SALSKFVEEQNLKDLRVWTSQLKSTIQTAEAL-R | 312 |
| Liver PFK-2 | LDSHLSYIKIFDVGTRYMVNRVQDHIQSRTVYYLMNIHVTPRSIYLCRHGESELN-IRGRIGGDSGLSVRGKQYA-YALANFIQSQGISSLKVWTSRMKRTIQTAEAL-G | 317 |
| iPFK-2 | LPYEQMKALNEIDAGVCEELTYEEIRDTYPEEYALREQDKY-YYRYPTGESYQDLVQRLEPVIMELERQENVLVICHQAVLRCLLAYFLDKSAEEMPYLKCPLHTVLKLT | 421 |
| Liver PFK-2 | VPYEQMKALNEIDAGVCEEMTYEEIQEHYPEEFALRDQDKYRY-RYPKGESYEDLVQRLEPVIMELERQENVLVICHQAVMRCLLAYFLDKSSDELPYLKCPLHTVLKLT | 426 |
| iPFK-2 | PVAYGCRVESIYLNVESV-CTHRER------SRG-CKE--GT. | 454 |
| Liver PFK-2 | PVAYGCKVESIYLNVEAV-NTHREKPENVDITRE-PEEALDTV | 467 |

FIG. 1

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: hiPFK-2 antisense (xi) SEQUENCE DESCRIPTION: SEQ ID NO:1:

AGCCGCGAAG ATGCCGTTGG                                                    20

(2) INFORMATION FOR SEQ ID NO:2:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: hiPFK-2 antisense (xi) SEQUENCE DESCRIPTION: SEQ ID NO:2:

CCAACGGCAT CTTCGCGGCT                                                    20

(2) INFORMATION FOR SEQ ID NO:3:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: hiPFK-2 antisense (xi) SEQUENCE DESCRIPTION: SEQ ID NO:3:

AAGATGCCGT TGGAACTGAC                                                    20

(2) INFORMATION FOR SEQ ID NO:4:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: hiPFK-2 antisense (xi) SEQUENCE DESCRIPTION: SEQ ID NO:4:

GTCAGTTCCA ACGGCATCTT                                                    20

(2) INFORMATION FOR SEQ ID NO:5:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:5:

TGAGGCAGAC GTGTCGGTTC                                                    20

(2) INFORMATION FOR SEQ ID NO:6:

(i) SEQUENCE CHARACTERISTICS:
        (A) LENGTH: 20
        (B) TYPE: nucleic acid (C) STRANDEDNESS: single
            (D) TOPOLOGY: unknown (ii) MOLECULE TYPE: PCR primer (xi) SEQUENCE DESCRIPTION: SEQ ID NO:6:

CAGCAGCTCC AGGAAAGTGT                                                    20

(2) INFORMATION FOR SEQ ID NO:7:

(i) SEQUENCE CHARACTERISTICS:
            (A) LENGTH: 20
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO:7:

TAAGGAGAAG CTGTGCTACG                                                    20

(2) INFORMATION FOR SEQ ID NO:8:

(i) SEQUENCE CHARACTERISTICS:
            (A) LENGTH: 20
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO:8:

ATCTCCTTCT GCATCCTGTC                                                    20

(2) INFORMATION FOR SEQ ID NO:9:

(i) SEQUENCE CHARACTERISTICS:
            (A) LENGTH: 20
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO:9:

ATTGGTCTGG CAACTGCAAA                                                    20

(2) INFORMATION FOR SEQ ID NO:10:

(i) SEQUENCE CHARACTERISTICS:
            (A) LENGTH: 20
            (B) TYPE: nucleic acid
            (C) STRANDEDNESS: single
            (D) TOPOLOGY: unknown (ii) MOLECULE TYPE: PCR primer (xi) SEQUENCE DESCRIPTION: SEQ ID NO:10:

GGAGCCTCCT ATGTGTGACT                                                    20

(2) INFORMATION FOR SEQ ID NO:11:

(i) SEQUENCE CHARACTERISTICS:
            (A) LENGTH: 4220 base pairs
            (B) TYPE: nucleic acid
            (C) STRANDEDNESS: single
            (D) TOPOLOGY: unknown (ii) MOLECULE TYPE: human iPFK-2

(xi) SEQUENCE DESCRIPTION: SEQ ID NO:11:

```
CAGGTCGAGC GGCAGGGCCT GGTGGCGAGA GCGCAGCCGC GAAGATGCCG         50
TTGGAACTGA CGCAGAGCCG AGTGCAGAAG ATCTGGGTGC CCGTGGACCA         100
CAGGCCCTCG TTGCCCAGAT CCTGTGGGCC AAAGCTGACC AACTCCCCCA         150
CCGTCATCGT CATGGTGGGC CTCCCCGCCC GGGGCAAGAC CTACATCTCC         200
AAGAAGCTGA CTCGCTACCT CAACTGGATT GGCGTCCCCA CAAAAGTGTT         250
CAACGTCGGG GAGTATCGCC GGGAGGCTGT GAAGCAGTAC AGCTCCTACA         300
ACTTCTTCCG CCCCGACAAT GAGGAAGCCA TGAAAGTCCG GAAGCAATGT         350
GCCCTAGCTG CCTTGAGAGA TGTCAAAAGC TACCTGGCGA AGAAGGGGG          400
ACAAATTGCG GTTTTCGATG CCACCAATAC TACTAGAGAG AGGAGACACA         450
TGATCCTCCA TTTTGGCAAA GAAATGACT  TTAAGGCGTT TTTCATCGAG         500
TCGGTGTGCG ACGACCCTAC AGTTGTGGCC TCCAATATCA TGGAAGTTAA         550
AATCTCCAGC CCGGATTACA AAGACTGCAA CTCGGCAGAA GCCATGGACG         600
ACTTCATGAA GAGGATCAGT TGCTATGAAG CCAGCTACCA GCCCCTCGAC         650
CCCGACAAAT GCGACAGGGA CTTGTCGCTG ATCAAGGTGA TTGACGTGGG         700
CCGGAGGTTC CTGGTGAACC GGGTGCAGGA CCACATCCAG AGCCGCATCG         750
TGTACTACCT GATGAACATC CACGTGCAGC CGCGTACCAT CTACCTGTGC         800
CGGCACGGCG AGAACGAGCA CAACCTCCAG GGCCGCATCG GGGCGACTC          850
AGGCCTGTCC AGCCGGGGCA AGAAGTTTGC CAGTGCTCTG AGCAAGTTCG         900
TGGAGGAGCA GAACCTGAAG GACCTGCGCG TGTGGACCAG CCAGCTGAAG         950
AGCACCATCC AGACGGCCGA GGCGCTGCGG CTGCCCTACG AGCAGTGGAA         1000
GGCGCTCAAT GAGATCGACG CGGGCGTCTG TGAGGAGCTG ACCTACGAGG         1050
AGATCAGGGA CACCTACCCT GAGGAGTATG CGCTGCGGGA GCAGGACAAG         1100
TACTATTACC GCTACCCCAC CGGGGAGTCC TACCAGGACC TGGTCCAGCG         1150
CTTGGAGCCA GTGATCATGG AGCTGGAGCG GCAGGAGAAT GTGCTGGTCA         1200
TCTGCCACCA GGCCGTCCTG CGCTGCCTGC TTGCCTACTT CCTGGATAAG         1250
AGTGCAGAGG AGATGCCCTA CCTGAAATGC CCTCTTCACA CCGTCCTGAA         1300
ACTGACGCCT GTCGCTTATG GCTGCCGTGT GGAATCCATC TACCTGAACG         1350
TGGAGTCCGT CTGCACACAC CGGGAGAGGT CAGAGGATGC AAAGAAGGGA         1400
CCTAACCCGC TCATGAGACG CAATAGTGTC ACCCCGCTAG CCAGCCCCGA         1450
ACCCACCAAA AAGCCTCGCA TCAACAGCTT TGAGGAGCAT GTGGCCTCCA         1500
CCTCGGCCGC CCTGCCCAGC TGCCTGCCCC CGGAGGTGCC CACGCAGCTG         1550
CCTGGACAAC CTTTGCTAGG GCAAGCCTGT CTAACATGAA AGGTTCCCGG         1600
AGCAGCGCTG ACTCCTCCAG GAAACACTGA GGCAGACGTG TCGGTTCCAT         1650
TCCATTTCCA TTTCTGCAGC TTAGCTTGTG TCCTGCCCTC CGCCCGAGGC         1700
AAAACGTATC CTGAGGACTT CTTCCGGAGA GGGTGGGGTG GAGCAGCGGG         1750
GGAGCCTTGG CCGAAGAGAA CCATGCTTGG CACCGTCTGT GTCCCCTCGG         1800
CCGCTGGACA CCAGAAAGCC ACGTGGGTCC CTGGCGCCCT GCCTTTAGCC         1850
GTGGGGCCCC CACCTCCACT CTCTGGGTTT CCTAGGAATG TCCAGCCTCG         1900
```

| | |
|---|---|
| GAGACCTTCA CAAAGCCTTG GGAGGGTGAT GAGTGCTGGT CCTGACAAGA | 1950 |
| GGCCGCTGGG GACACTGTGC TGTTTTGTTT CGTTTCTGTG ATCTCCCGGC | 2000 |
| ACGTTTGGAG CTGGGAAGAC CACACTGGTG GCAGAATCCT AAAATTAAAG | 2050 |
| GAGGCAGGCT CCTAGTTGCT GAAAGTTAAG GAATGTGTAA AACCTCCACG | 2100 |
| TGACTGTTTG GTGCATCTTG ACCTGGGAAG ACGCCTCATG GGAACGAACT | 2150 |
| TGGACAGGTG TTGGGTTGAG GCCTCTTCTG CAGGAAGTCC CTGAGCTGAG | 2200 |
| ACGCAAGTTG GCTGGGTGGT CCGCACCCTG GCTCTCCTGC AGGTCCACAC | 2250 |
| ACCTTCCAGG CCTGTGGCCT GCCTCCAAAG ATGTGCAAGG GCAGGCTGGC | 2300 |
| TGCACGGGGA GAGGGAAGTA TTTTGCCGAA ATATGAGAAC TGGGGCCTCC | 2350 |
| TGCTCCCAGG GAGCTCCAGG GCCCCTCTCT CCTCCCACCT GGACTTGGGG | 2400 |
| GGAACTGAGA AACACTTTCC TGGAGCTGCT GGCTTTTGCA CTTTTTTGAT | 2450 |
| GGCAGAAGTG TGACCTGAGA GTCCCACCTT CTCTTCAGGA ACGTAGATGT | 2500 |
| TGGGGTGTCT TGCCCTGGGG GGCTTGGAAC CTCTGAAGGT GGGGAGCGGA | 2550 |
| ACACCTGGCA TCCTTCCCCA GCACTTGCAT TACCGTCCCT GCTCTTCCCA | 2600 |
| GGTGGGGACA GTGGCCCAAG CAAGGCCTCA CTCGCAGCCA CTTCTTCAAG | 2650 |
| AGCTGCCTGC ACACTGTCTT GGAGCATCTG CCTTGTGCCT GGCACTCTGC | 2700 |
| CGGTGCCTTG GGAAGGTCGG AAGAGTGGAC TTTGTCCTGG CCTTCCCTTC | 2750 |
| ATGGCGTCTA TGACACTTTT GTGGTGATGG AAAGCATGGG ACCTGTCGTC | 2800 |
| TCAGCCTGTT GGTTTCTCCT CATTGCCTCA AACCCTGGGG TAGGTGGGAC | 2850 |
| GGGGGGTCTC GTGCCCAGAT GAAACCATTT GGAAACTCGG CAGCAGAGTT | 2900 |
| TGTCCAAATG ACCCTTTTCA GGATGTCTCA AAGCTTGTGC CAAAGGTCAC | 2950 |
| TTTTCTTTCC TGCCTTCTGC TGTGAGCCCT GAGATCCTCC TCCCAGCTCA | 3000 |
| AGGGACAGGT CCTGGGTGAG GGTGGGAGAT TTAGACACCT GAAACTGGGC | 3050 |
| GTGGAGAGAA GAGCCGTTGC TGTTTGTTTT TTGGGAAGAG CTTTTAAAGA | 3100 |
| ATGCATGTTT TTTTCCTGGT TGGAATTGAG TAGGAACTGA GGCTGTGCTT | 3150 |
| CAGGTATGGT ACAATCAAGT GGGGGATTTT CATGCTGAAC CATTCAAGCC | 3200 |
| CTCCCCGCCC GTTGCACCCA CTTTGGCTGG CGTCTGCTGG AGAGGATGTC | 3250 |
| TCTGTCCGCA TTCCCGTGCA GCTCCAGGCT CGCGCAGTTT TCTCTCTCCC | 3300 |
| CCTGGATGTT GAGTCTCATC AGAATATGTG GTAGGGGGT GGACGTGCAC | 3350 |
| GGGTGCATGA TTGTGCTTAA CTTGGTTGTA TTTTTCGATT TGACATGGAA | 3400 |
| GGCCTGTTGC TTTGCTCTTG AGAATAGTTT CTCGTGTCCC CCTCGCAGGC | 3450 |
| CTCATTCTTT GAACATCGAC TCTGAAGTTT GATACAGATA GGGGCTTGAT | 3500 |
| AGCTGTGGTC CCCCTCTCCC CTCTGACTAC CTAAAATCAA TACCTAAATA | 3550 |
| CAGAAGCCTT GGTCTAACAC GGGACTTTTA GTTTGCGAAG GGCCTAGATA | 3600 |
| GGGAGAGAGG TAACATGAAT CTGGACAGGG AGGGAGATAC TATAGAAAGG | 3650 |
| AGAACACTGC CTACTTTGCA AGCCAGTGAC CTGCCTTTTG AGGGGACATT | 3700 |
| GGACGGGGGC CGGGGCGGG GGTTGGGTTT GAGCTACAGT CATGAACTTT | 3750 |
| TGGCGTCTAC TGATTCCTCC AACTCTCCAC CCCACAAAAT AACGGGGACC | 3800 |
| AATATTTTTA ACTTTGCCTA TTTGTTTTTG GGTGAGTTTC CCCCCTCCTT | 3850 |
| ATTCTGTCCT GAGACCACGG GCAAAGCTCT TCATTTTGAG AGAGAAGAAA | 3900 |

| | |
|---|---|
| AACTGTTTGG AACCACACCA ATGATATTTT TCTTTGTAAT ACTTGAAATT | 3950 |
| TATTTTTTTA TTATTTTGAT AGCAGATGTG CTATTTATTT ATTTAATATG | 4000 |
| TATAAGGAGC CTAAACAATA GAAAGCTGTA GAGATTGGGT TTCATTGTTA | 4050 |
| ATTGGTTTGG GAGCCTCCTA TGTGTGACTT ATGACTTCTC TGTGTTCTGT | 4100 |
| GTATTTGTCT GAATTAATGA CCTGGGATAT AAAGCTATGC TAGCTTTCAA | 4150 |
| ACAGGAGATG CCTTTCAGAA ATTTGTATAT TTTGCAGTTG CCAGACCAAT | 4200 |
| AAAATACCTG GTTGAAATAC | 422 0 |

(2) INFORMATION FOR SEQ ID NO:12:

(i) SEQUENCE CHARACTERISTICS:
        (A) LENGTH: 13
        (B) TYPE: nucleic acid
        (C) STRANDEDNESS: single
        (D) TOPOLOGY: unknown (ii) MOLECULE TYPE: query sequence (xi) SEQUENCE DESCRIPTION: SEQ ID NO:12:

| | |
|---|---|
| ATTTATTTAT TTA | 13 |

(2) INFORMATION FOR SEQ ID NO:13:

(i) SEQUENCE CHARACTERISTICS:
        (A) LENGTH: 28
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:13:

| | |
|---|---|
| GATTGTACCA TACCTGAAGC ACAGCCTC | 28 |

(2) INFORMATION FOR SEQ ID NO:14:

(i) SEQUENCE CHARACTERISTICS:
        (A) LENGTH: 28
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:14:

| | |
|---|---|
| TCTCCTGCCG CTCCAGCTCC ATGATCAC | 28 |

(2) INFORMATION FOR SEQ ID NO:15:

(i) SEQUENCE CHARACTERISTICS:
        (A) LENGTH: 28
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:15:

| | |
|---|---|
| GTCAGCTTCT TGGAGATGTA GGTCTTGC | 28 |

(2) INFORMATION FOR SEQ ID NO:16:

(i) SEQUENCE CHARACTERISTICS:

(A) LENGTH: 28
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:16:

TTGGTTTGGG AGCCTCCTAT GTGTGACT                                              28

(2) INFORMATION FOR SEQ ID NO:17:

(i) SEQUENCE CHARACTERISTICS:
        (A) LENGTH: 28
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:17:

TTGGCGTCTA CTGATTCCTC CAACTCTC                                              28

(2) INFORMATION FOR SEQ ID NO:18:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:18:

CTGTACCTGT CCTGCGTGTT                                                       20

(2) INFORMATION FOR SEQ ID NO:19:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:19:

AGCTCTCTTT AGGAAGACAC                                                       20

(2) INFORMATION FOR SEQ ID NO:20:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:20:

GAAGTCAAAC TGAATGTGTC                                                       20

(2) INFORMATION FOR SEQ ID NO:21:

(i) SEQUENCE CHARACTERISTICS:
        (A) LENGTH: 20
        (B) TYPE: nucleic acid
        (C) STRANDEDNESS: single
        (D) TOPOLOGY: unknown (ii) MOLECULE TYPE: PCR primer (xi) SEQUENCE DESCRIPTION: SEQ ID NO:21:

CCTCTTGTAG GCAGTAAGTC                                                       20

(2) INFORMATION FOR SEQ ID NO:22:

(i) SEQUENCE CHARACTERISTICS:
             (A) LENGTH: 20
             (B) TYPE: nucleic acid
             (C) STRANDEDNESS: single
             (D) TOPOLOGY: unknown (ii) MOLECULE TYPE: PCR primer (xi) SEQUENCE DESCRIPTION: SEQ ID NO:22:

AGGCAGTAAG TCTTTATTCG                                                       20

(2) INFORMATION FOR SEQ ID NO:23:

(i) SEQUENCE CHARACTERISTICS:
             (A) LENGTH: 20
             (B) TYPE: nucleic acid
             (C) STRANDEDNESS: single
             (D) TOPOLOGY: unknown (ii) MOLECULE TYPE: PCR primer (xi) SEQUENCE DESCRIPTION: SEQ ID NO:23:

AAGTCAAACT GCCTGTGTCC                                                       20

(2) INFORMATION FOR SEQ ID NO:24:

(i) SEQUENCE CHARACTERISTICS:
             (A) LENGTH: 12
             (B) TYPE: amino acid
             (C) STRANDEDNESS: single
             (D) TOPOLOGY: unknown (ii) MOLECULE TYPE: polypeptide (xi) SEQUENCE DESCRIPTION: SEQ ID NO:24:

His Arg Glu Arg Ser Arg Gly Cys Lys Glu G ly Thr
                 5                   10

(2) INFORMATION FOR SEQ ID NO:25:

(i) SEQUENCE CHARACTERISTICS:
             (A) LENGTH: 20
             (B) TYPE: nucleic acid
             (C) STRANDEDNESS: single
             (D) TOPOLOGY: unknown (ii) MOLECULE TYPE: PCR primer (xi) SEQUENCE DESCRIPTION: SEQ ID NO:25:

TGAGGCAGAC GTGTCGGTTC                                                       20

(2) INFORMATION FOR SEQ ID NO:26:

(i) SEQUENCE CHARACTERISTICS:
             (A) LENGTH: 20
             (B) TYPE: nucleic acid
             (C) STRANDEDNESS: single
             (D) TOPOLOGY: unknown (ii) MOLECULE TYPE: PCR primer -continued (xi) SEQUENCE DESCRIPTION: SEQ ID NO:26:

CAGCAGCTCC AGGAAAGTGT                              20

INDUCIBLE PHOSPHOFRUCTOKINASE AND THE WARBURG EFFECT

TECHNICAL FIELD OF THE INVENTION

The present invention provides a novel phosphofructokinase (iPFK-2) isozyme that is preferentially transcribed and translated in tumor cells. The discovery of this isozyme, together with its function, led to the discovery of its use as a diagnostic target, as a drug screening target, and antisense compounds that inhibit its translation in cellular cytosol as an anti-tumor treatment.

BACKGROUND OF THE INVENTION

The glycolytic pathway is a fundamental anaerobic pathway for sugar metabolism in eukaryotic cells. Glycolysis has a dual role, to degrade sugars to generate energy (ATP) and to provide building blocks for synthetic reactions. The rate of conversion of glucose into pyruvate is regulated to meet these two major cellular needs. In glycolysis, the enzymes hexokinase, phosphofructokinase and pyruvate kinase catalyze irreversible reactions and are regulated enzymes for control points in glycolysis. The enzymes are regulated by reversible binding of allosteric effectors, by covalent modification and by transcriptional control to meet changing metabolic needs. Of the three control enzymes, phosphofructokinase is the most important control point in mammalian glycolysis.

In 1930, Warburg pointed out that tumors have a high rate of anaerobic glycolysis and that they do not show a decreased glycolytic rate at relatively high $O_2$ concentrations. This loss of regulatory control (i.e., the Pasteur effect) has come to be called the Warburg effect. Supplying tumor cells with glucose results in an inhibition of oxygen consumption, which magnifies the dependence on glucose for energy. Other cellular types do not normally show this effect since they maintain respiration from other substrates even in the presence of glucose. The question of why rapidly growing tumors have a marked tendency to convert the glycolytically-generated pyruvate to lactic acid in the cytosol instead of transporting into the mitochondria for total oxidation has puzzled biochemists for years. The physiologic consequence of this altered metabolic behavior are clear. Tumor tissue generates a high degree of metabolic inefficiency in the host, through an enhanced operation of energy-wasting processes, such as the Cori cycle between the tumor and the liver. As a result of the high glycolytic rate, a large amount of pyruvate is generated, together with an increase in the cytosolic NADH/NAD+ratio, which favors the reduction of pyruvate to lactate through the action of lactate dehydrogenase. This is also supported by the low mitochondrial content of tumor cells which hampers the possibility of dissipating NADH through the action of the electron transfer chain and the low levels of NADH-shuttle systems found in a great number of tumors. The tumor cell becomes a lactate exporter in a similar way to some muscular fibers in anoxic situations. Although the precise role of the enhanced Cori cycle in tumor-bearing states is not fully determined, it adds inefficiency to the host in a way that, instead of ATP formation of 36–38 molecules during the complete oxidation of glucose to $CO_2$, a net loss of 4 ATPs can be expected when two three-carbon molecules are converted to one molecule of glucose.

A distinctive metabolic environment of cancer-bearing individuals has been described (Argilés and Azcón-Bieto, Mol. Cell. Biochem. 81:3–17, 1988). Tumor invasion upon a host has been metabolically characterized by a reduction of the metabolic efficiency of the host, muscular protein depletion, increased gluconeogenesis, and uncoupling of oxidative phosphorylation. The net result is an energy imbalance leading to cachexia and eventual starvation.

SUMMARY OF THE INVENTION

The present invention provides a cancer malignancy diagnostic assay comprising obtaining a sample of a body fluid or tissue, performing a sequence identity assay to look for the presence of iPFK-2 specific sequences (SEQ ID NO: 11). Preferably, the sequence identity assay is selected from the group consisting of PCR (polymerase chain reaction) assays, ELISA immunologic assays, hybridization assays, and combinations thereof. The present invention further provides an anticancer, anti-inflammatory and cachexia pharmaceutical composition comprising a specific antisense oligonucleotide to the inventive isolated iPFK-2 sequence and a pharmaceutically acceptable oligonucleotide carrier. Preferably, the antisense oligonucleotide is selected from a 15–50 base oligonucleotide incorporating an oligonucleotide sequence selected from the group consisting of):
5'-AGCCGCGAAGATGCCGTTGG-3'[SEQ ID NO: 1],
5'-CCAACGGCATCTTCGCGGCT-3'[SEQ ID NO: 2],
5'-AAGATGCCGTTGGAACTGAC-3'[SEQ ID NO: 3],
5'-GTCAGTTCCAACGGCATCTT-3'[SEQ ID NO: 4], and combinations thereof. The present invention further provides a therapeutic agent screening assay to screen for compounds having anti-tumor activity, comprising: (a) obtaining recombinant iPFK-2 having activity that forms fructose 2,6-diphosphate from fructose 6-phosphate substrate: (b) adding candidate drug at various concentrations or no-drug control vehicle; and (c) assaying for fructose 2,6-diphosphate as a measure of enzymatic activity. Preferably, the product assay is conducted by means of an enzymatic assay.

The present invention further provides a recombinant iPFK-2 polypeptide expressed by the cDNA sequence provided in SEQ ID NO. 11. The use of the iPFK-2 polypeptide, with known antibody techniques, including known monoclonal antibody techniques, further provides an antibody that specifically binds to iPFK-2. Preferably, this antibody is a monoclonal antibody.

BRIEF DESCRIPTION OF THE FIGURES

FIG. 1 shows an amino acid sequence alignment between human iPFK-2 (SEQ ID NO: 11) and human liver PFK-2. (|), identity; (:), favorable match; (.), neutral mismatch; ( ), unfavorable mismatch.

FIG. 2A shows a RT-PCR analysis. FIG. 2B shows a Northern blot analysis. FIG. 2C shows a Western blot analysis.

FIG. 3A shows a Northern blot analysis of various human cancer cell lines. FIG. 3B shows a RT-PCR analysis of K-562 cells for β-actin, iPFK-2 and human liver PFK-2.

FIG. 4A shows a Western blot analysis of the iPFK2 antagonist activity of the antisense oligonucleotide. FIG. 4B shows a fructose-2,6-bisphosphate assay of the iPFK2 antagonist activity of the antisense oligonucleotide(AS) versus the sense (S) sequence. FIG. 4C shows a 5-phosphoribosyl 1-pyrophosphate assay and a K562 cell proliferation assay of the iPFK2 antagonist activity of the antisense oligonucleotide(AS) versus the sense (S) sequence.

DETAILED DESCRIPTION OF THE INVENTION

Figure 2A:
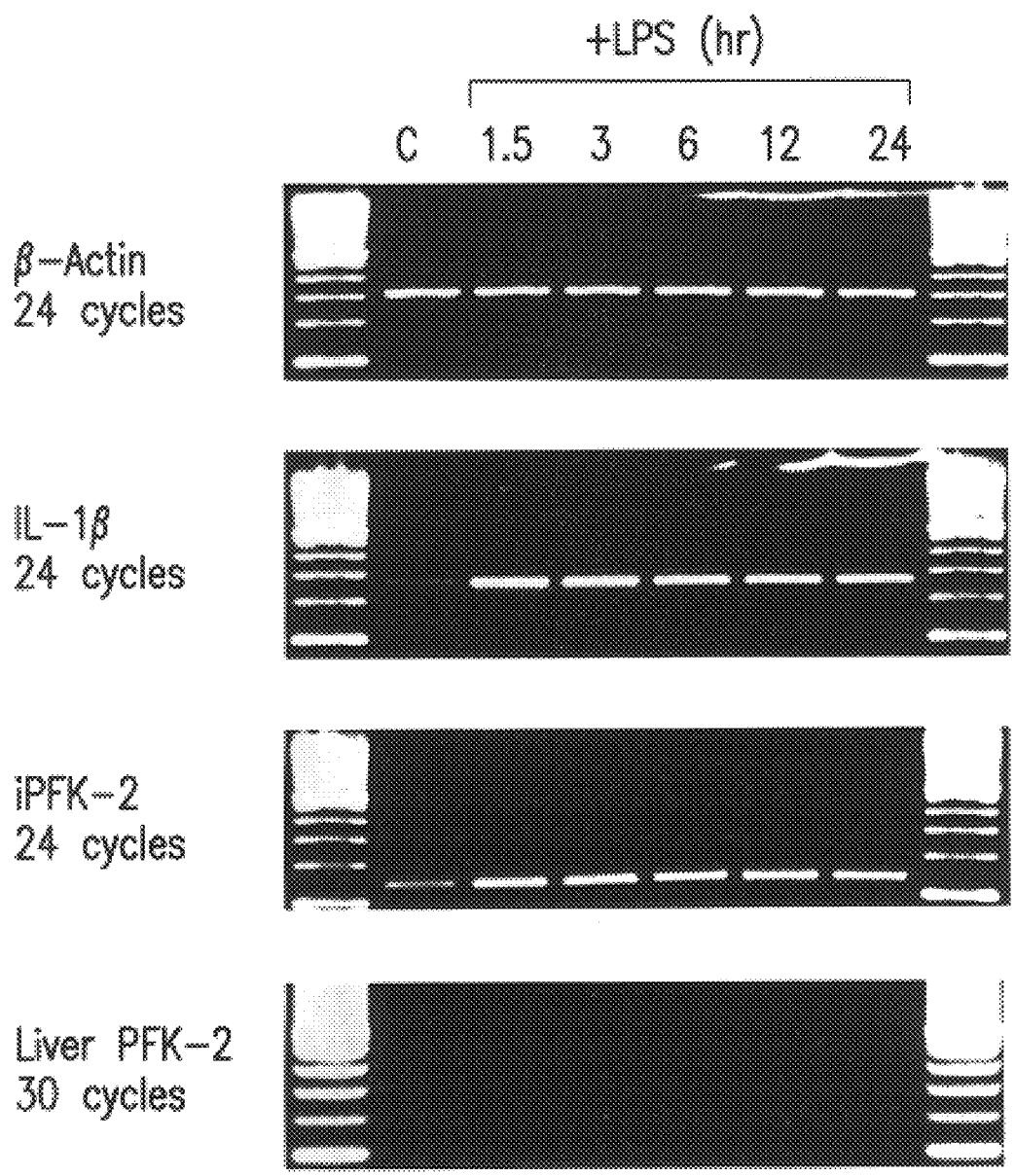
FIGS. 2A–C show that LPS induces peripheral blood monocytes to rapidly express iPFK-2 mRNA and protein.

The present invention provides a cancer malignancy diagnostic assay comprising obtaining a sample of a body or tumor fluid or tissue, and performing a sequence identity assay to look for the presence of iPFK-2 specific sequences. Preferably, the sequence identity assay is selected from the group consisting of PCR (polymerase chain reaction) assays, ELISA immunologic assays, hybridization assays, and combinations thereof. The present invention further provides an anticancer pharmaceutical composition comprising an antisense oligonucleotide specific to the inventive isolated PFK-2 sequence and a pharmaceutically acceptable oligonucleotide carrier. Preferably, the antisense oligonucleotide is selected from a 15–50 base oligonucleotide incorporating an oligonucleotide sequence selected from the group consisting of): 5'-AGCCGCGAAGATGCCGTTGG-3'[SEQ ID NO: 1], 5'-CCAACGGCATCTTCGCGGCT-3'[SEQ ID NO: 2], 5'-AAGATGCCGTTGGAACTGAC-3'[SEQ ID NO: 3], 5'-GTCAGTTCCAACGGCATCTT-3'[SEQ ID NO: 4], and combinations thereof.

The present invention further provides a recombinant iPFK-2 polypeptide expressed by the cDNA sequence provided in SEQ ID NO. 11. The use of the iPFK-2 polypeptide, with known antibody techniques, including known monoclonal antibody techniques, further provides an antibody that specifically binds to iPFK-2. Preferably, this antibody is a monoclonal antibody.

The present invention further provides an isolated cDNA sequence encoding an inducible human phosphofructokinase-2 (iPFK-2) enzyme. The cDNA sequence is listed as SEQ ID NO 11 and in FIG. 1. SEQ ID NO. 11 provides a bolded start and stop codon of the coding region. Further, there are underlined base pairs at the C terminal region of the coding region that provide additional amino acids not found in any other PFK-2 isotypes. The inventive iPFK-2 cDNA sequence is useful for producing recombinant iPFK-2 polypeptide, for designing antisense oligonucleotides, and for transfecting cells (both prokaryotic and eukaryotic) to produce recombinant iPFK-2 and fragments thereof. The recombinant iPFK-2 polypeptide, having PFK-2 enzymatic activity, is useful for screening for inhibitors having therapeutic activity as anticancer agents specifically against the inventive inducible iPFK-2 isoform. Anti-cancer therapeutic activity can be attributable to iPFK-2 inhibitors because a novel, AU-rich early response gene is required for leukemia growth. This gene appears to be the inducible iPFK-2 gene, the gene product of which is most prevalent in tumor cells.

The present invention further provides an isolated cDNA sequence encoding an inducible human phosphofructokinase-2 (iPFK-2) isozyme. The examples below detail the efforts that led to the isolation, purification and expression of this isozyme. The isolated isozyme sequence was found to be preferentially expressed in tumor cells and lead to increased glycolytic activity.

The invention is based upon the identification and understanding of a novel gene for PFK-2/FBPase (6-phosphofructo-2-kinase (PFK-2)/fructose-2,6-biphosphophatase (FBPase) or "iPFK-2" that is induced by pro-inflammatory stimuli and which is distinguished from other similar genes encoding PFK-type enzymes by the presence of multiple copies of an AUUUA mRNA instability motif in its 3'-untranslated end. This AU-rich element is characteristic of mRNAs encoding several inflammatory cytokines (e.g., TNFα, IL-1, IFN-γ, and GM-CSF) and oncoproteins (e.g., c-Fos, c-Myc, and c-Sis) (Greenberg and Belasco, in *Control of Messenger RNA Stability*, Belasco and Brawerman eds., pp. 199–218, Academic Press, New York, 1993). Data presented herein shows that iPFK-2 is expressed constitutively in several human cancer cell lines and was found to be essential for tumor cell growth in vivo. Inhibiting the level of iPFK-2 protein expression (through the use of antisense antagonists) decreased intracellular levels of 5-phosphoribosyl-1-pyrophosphate (PRPP), an important precursor for purine and pyrimidine biosynthesis. Accordingly, iPFK-2 is an important regulatory isoenzyme that appears to be essential for tumor growth, whose antagonists have important anti-cancer therapeutic activity, and provides an explanation for long-standing observations concerning the apparent coupling of glycolysis and cancer cell proliferation.

The mRNAs of several cytokines and proto-oncogenes that are members of early response gene families have been noted to contain the sequence motif AUUUA in their 3' untranslated region (3'UTR). This AU-rich element confers instability to the mRNA molecule and plays a role in regulating its physiologic half life (Caput et al., *Proc. Natl. Acad. Sci. USA* 83:1670–1674, 1986; and Shaw et al., *Cell* 46: 659–667, 1986). An expressed sequence tag (EST)

database was searched for cDNA sequences containing conserved AUUUA sequence motifs. One AU-rich EST, unrelated to previously described genes, was identified and the complete cDNA was cloned and sequenced. The DNA sequence of this novel gene was found to share 29% identity with human liver PFK-2 (FIG. 1), which does not contain AU-rich elements. The predicted amino acid sequence showed 69% identity and extensive conservative substitutions (FIG. 1) (Lange and Pilkis, *Nucl. Acids Res.* 18:3652, 1990).

Figure 2B:
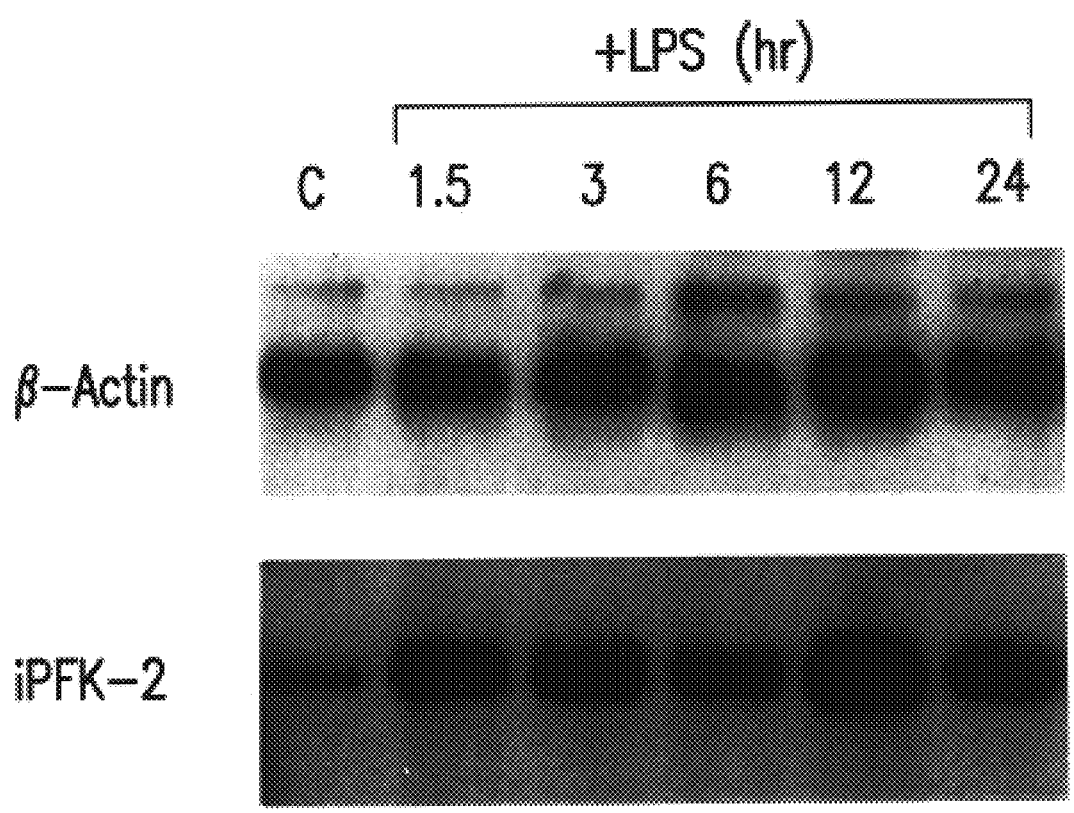
Figure 2C:
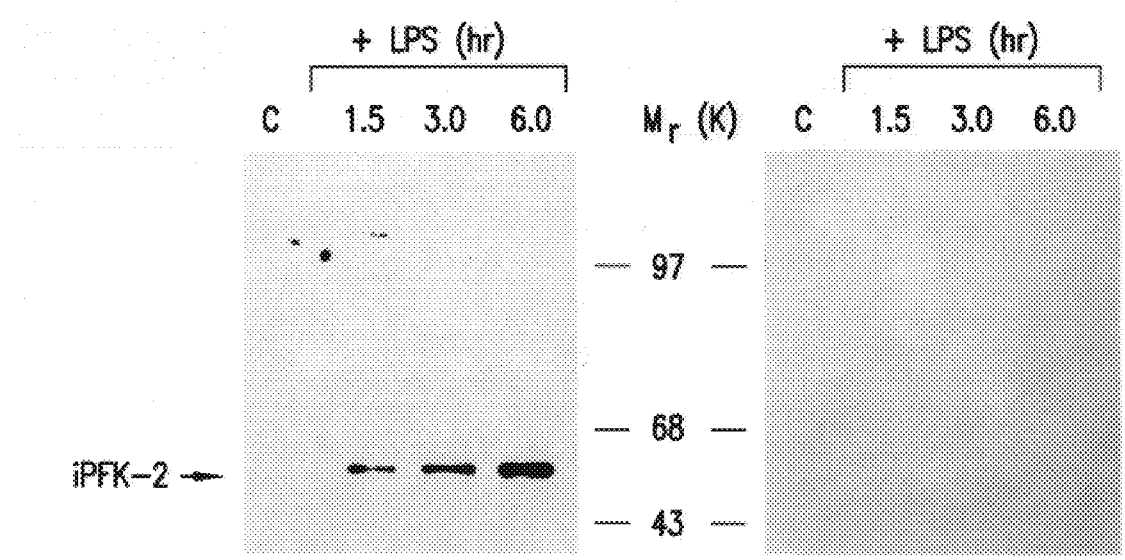

The expression of many proto-oncogenes and cytokines bearing the AUUUA motif increases in cells as a consequence of mitogenic or pro-inflammatory stimulation. Thus, only very low levels of iPFK-2 expression were detected by Northern blotting of normal human tissues (i.e., heart, brain, placenta, lung, liver, skeletal muscle, kidney, pancreas, spleen and lymph node). Northern analysis of human monocytes stimulated with lipopolysaccharide (LPS), by contrast, showed that the expression of this novel iPFK-2 gene was rapidly induced (FIG. 2A), hence the term "iPFK-2." The induction and increase in the level of iPFK-2 expression was similar to that which was observed for the cytokine IL-1β (which also contains AU-rich elements) (FIG. 2B). The expression of the liver (constitutive) isoform of PFK-2 was unaffected by LPS stimulation. Induction of iPFK-2 mRNA was accompanied by a corresponding increase in immunoreactive iPFK-2 protein, as measured by Western blotting analysis utilizing a specific anti-iPFK-2 antibody (FIG. 2C). These data demonstrate that iPFK-2, like other genes with AU-rich motifs in their 3'UTR, is induced in primary human monocytes upon pro-inflammatory activation in vitro. In a separate experiment, iPFK-2 expression in peripheral blood leukocytes of 5 HIV-infected patients was examined. In each case, the level of iPFK-2 mRNA was higher than that observed in control, uninfected individuals (n=3). These data suggest that iPFK-2 is induced upon leukocyte activation in vivo.

Figure 3A:
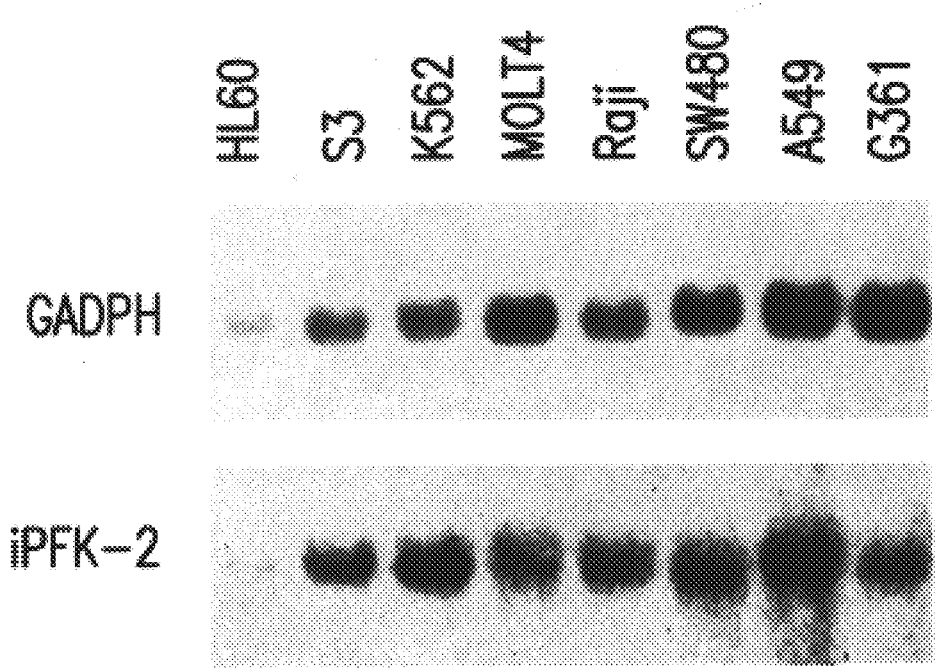
FIGS. 3A–B show iPFK-2 mRNA expression by human cancer cell lines.
Figure 3B:
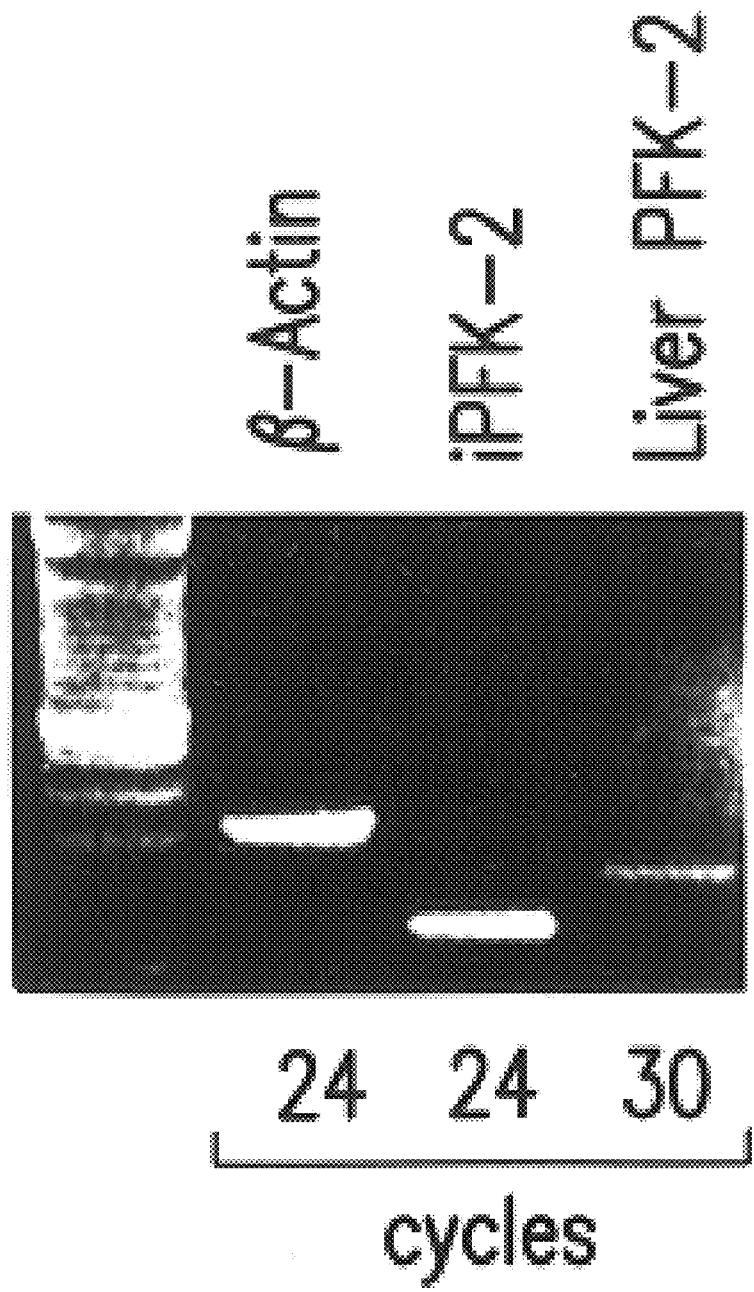

An increase in the level of stable expression of proto-oncogenes with AU-rich 3'UTR's is a characteristic feature of many transformed cells and can be directly oncogenic (Lee et al., *Mol. Cell. Biol.* 8:5521–5527, 1988; Rabbitts et al., *EMBO J.* 4:3727–3733, 1985; and Piechaczyk et al., *Cell* 42:589–597, 1985). Eight human tumor cell lines were examined for iPFK-2 mRNA by Northern blotting and high levels of expression were found (FIG. 3A). The intensities of iPFK-2 hybridization signals were comparable to iPFK-2 signals observed in the RNA obtained from LPS-stimulated primary human monocytes (FIG. 2B). Closer examination of the K562 chronic myelogenous leukemia cell line showed that the expression of iPFK-2 was much higher than that of the hepatic PFK-2 isoform (FIG. 3B). These data suggest that iPFK-2 expression is important in regulating the glycolytic pathway during tumor cell growth.

Figure 4A:
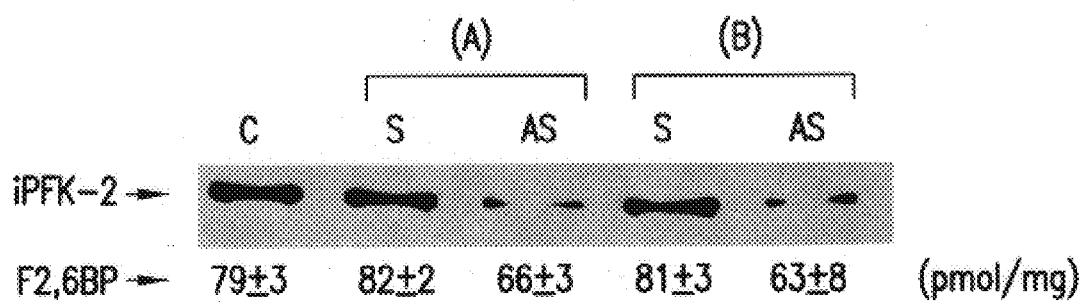
FIGS. 4A–C show that an iPFK-2 antagonist antisense oligonucleotide inhibited IPFK-2-specific K562 cell proliferation in vitro. Specifically.
Figure 4B:
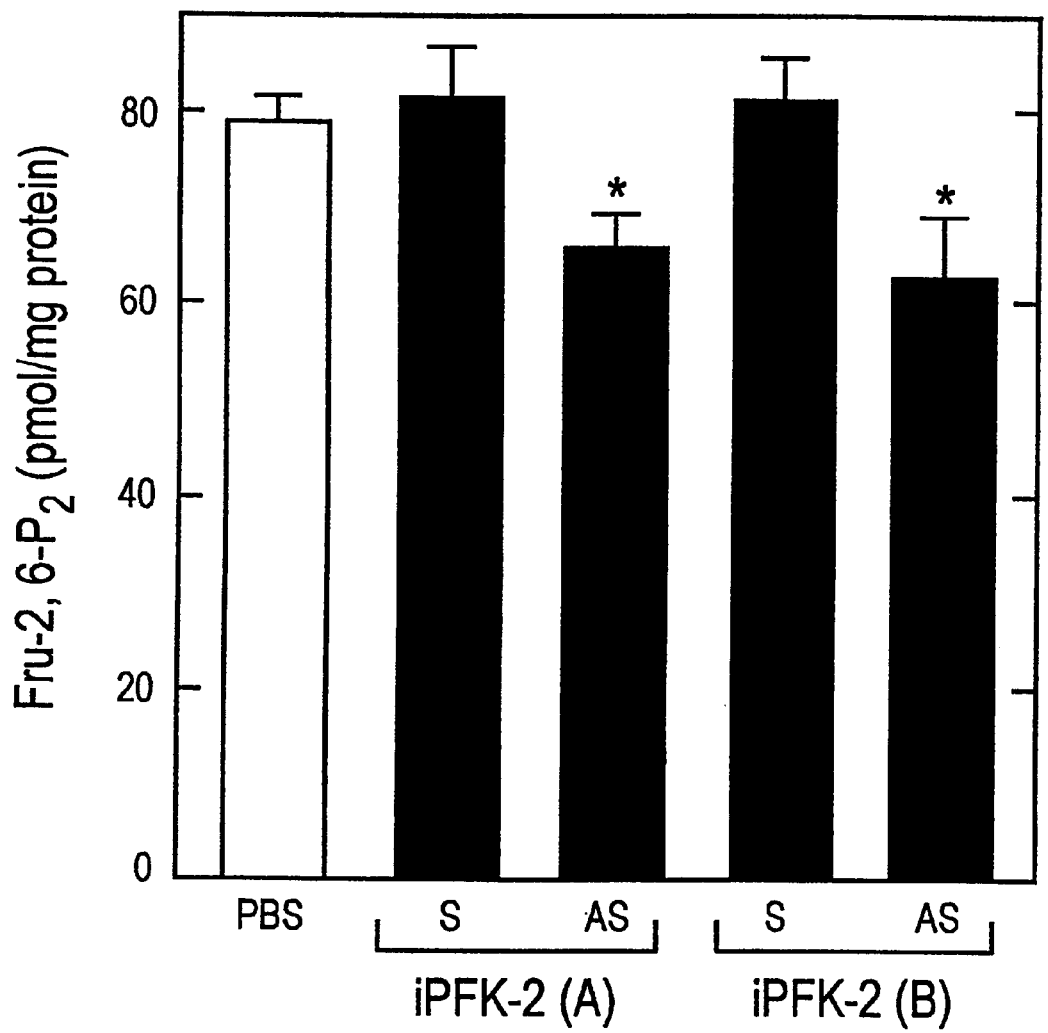

K562 leukemia cells were transfected with iPFK-2-specific anti-sense oligonucleotides. Both iPFK-2 protein and F2,6BP levels were significantly decreased when compared to cells transfected with oligonucleotide controls (FIG. 4A). These data indicate that the kinase activity of iPFK-2 contributes significantly to intracellular F2,6BP levels. The enhanced glycolytic flux in transformed cells facilitates the biosynthesis of 5-phosphoribosyl pyrophoshate (PRPP), a critical precursor for purine and pyrimidine biosynthesis (Eigenbrodt et al., *Trends Pharmacol. Sci.*, 1:240–245, 1980). Inhibition of iPFK-2 was found to significantly decrease PRPP levels in K562 cells and this decrease was associated with a corresponding decrease in K562 DNA synthesis and cell proliferation (FIG. 4B). A similar level of inhibition of DNA synthesis was observed after the transfection of iPFK-2 anti-sense oligonucleotides into HL-60, MOLT-4, SW480, G361, and KG1A cell lines. These observations indicate that iPFK-2 catalyzed F2-6BP production may enhance glycolytic flux (through formation of PFK-1) and permit increased channeling of glucose metabolism in the direction of PRPP synthesis.

Figure 4C:
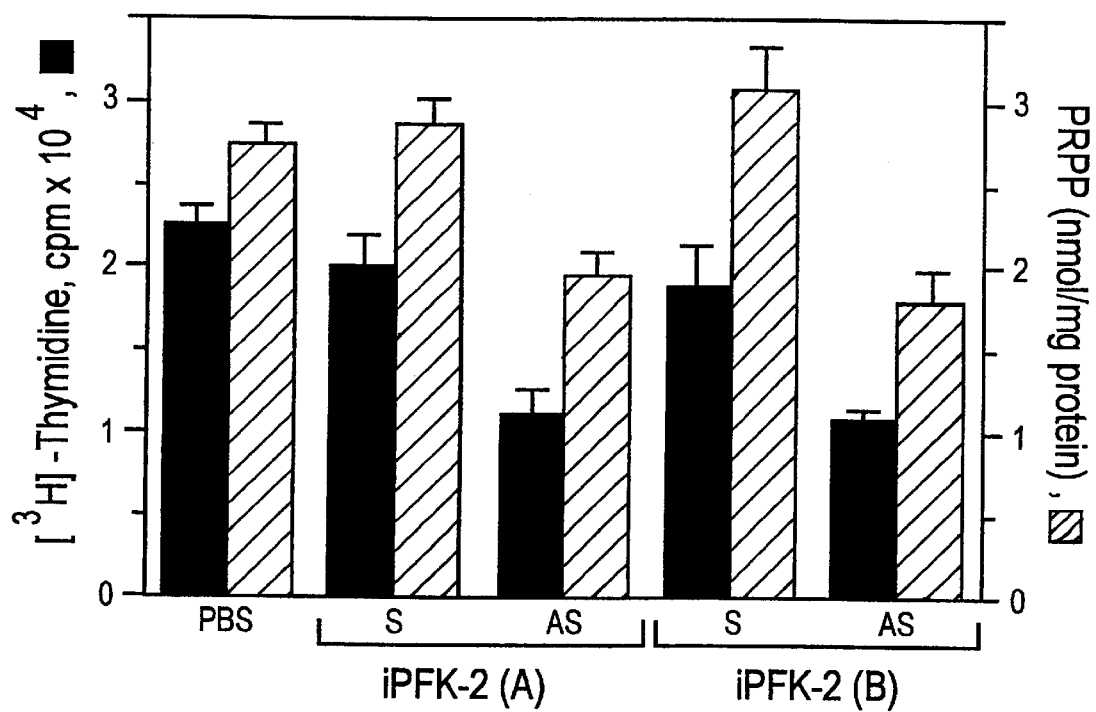

The role of iPFK-2 in tumorigenesis in vivo was examined by administering iPFK-2-specific antisense oligonucleotides to K562 tumor-bearing nude mice. Within 2 days of treatment, tumors for the iPFK-2 antisense-treated mice were significantly smaller than tumors from the iPFK-2 sense oligonucleotide or PBS-treated mice (FIG. 4C).

Fructose 2,6-bisphophate Assay

This illustrates a procedure to test for iPFK-2 inhibitors in a rapid in vitro assay suitable for high throughput screening of compounds or libraries of compounds. Confluent L6 cells were trypsinized, plated at $2 \times 10^5$ cells/ml in 6-wells plates and then incubated overnight at 37° C. The next day, medium was aspirated and replaced with 2 ml/well of differentiation medium (1% FBS DMEM+0.3 μM insulin). Cells were incubated overnight at 37° C. to allow for differentiation. Medium was then aspirated and the cells were washed twice with DMEM w/o FBS, stimulated with TNF (from 1 to 100 ng/ml), with MIF (from 10 to 1000 ng/ml) and/or treated with drugs or controls. At different times, medium was collected and the cells were lysed by adding 400 μl water+400 μl 0.1 M NaOH, and pipetting several times to mix. The lysates obtained can be used immediately or frozen for continued assay at a later time.

The lysates were prepared by transferring to eppendorf tubes, vortexed briefly, and incubated 80° C., 10 min. Tubes were spun 10 min at 14000 rpm and supernatants were transferred to new tubes and placed on ice. Added to the tubes was 3–4 μl ice-cold acetic acid, 1 M, in the presence of Hepes, 20 mM, to neutralize at pH ~7.5. The tubes were centrifuged for 10 min at 14000 rpm and the supernatants transferred to new tubes. The samples were ready to be assayed.

The following were added successively into a quartz cuvette: 0.5 ml 2×buffer solution (Tris/acetate buffer, 100 mM; Magnesium acetate, 4 mM; Fructose-6-Phosphate, 100 mM, and NADH, 0.3 mM); 0.1 ml 10×enzyme solution (Aldolase, 4.5 U/ml; Glycerol-3-P-dehydrogenase, 17 U/ml; Triosephosphate isomerase, 50 U/ml; Fructose bisphosphate kinase pyrophosphate dependent, 0.1 U/ml; make the solution in 0.2% BSA (final)); and 0.35 ml of the test sample or standard. The mixture was inverted with a parafilm cover and incubated for 5 min at room temperature in 0.05 ml pyrophosphate solution (Pyrophosphate, 10 mM). The mixture was mixed and absorbance read at 1 min intervals for 10 min, yielding $\Delta A/\Delta t$. Results were read off the concentration of the samples from a standard curve (fructose 2,6-bisphosphate, from $10^{-9}$ M). The foregoing assay can also be performed in smaller volumes, such as in multiple-well assay plates, so long as the same relative concentrations of reagents and enzymes are maintained.

Alternatively, Fructose 2,6-bisphosphate can be also measured in K562 cancer cells, which have constitutively high levels of this metabolite, in order to screen potential inhibitory compounds. K562 cells can be cultured in RPMI/10% FBS, following a similar protocol (see, for example, Van Schaftingen et al., *Eur. J. Biochem.* 129:191–195, 1982).

EXAMPLE 1

This example illustrates the initial cloning of the iPFK-2 sequence. An expressed sequence tag (EST) containing an AU-rich element was identified in the dbEST database at the National Center for Biotechnology Information by performing a TBLASTN search using the query sequence ATT-TATTTATTTA [SEQ ID NO.: 12]. AU-rich EST (GenBank ID F00287) had been obtained from a Homo sapiens skeletal muscle cDNA library and was unrelated to previously identified sequences. 5'- and 3'-rapid amplification of complementary DNA ends (RACE) was performed using a Human Skeletal Muscle Marathon cDNA-ready RACE kit (Clontech Laboratories, Inc., Palo Alto, Calif.). Gene-specific oligonucleotides used for sequential 5'-directed RACE include 5'-ATTGGTCTGGCAACTGCAAA-3'[SEQ ID NO.: 19], 5'-GATTGTACCATACCTGAAGCACAGCCTC-3'[SEQ ID NO.: 13], 5'TCTCCTGCCGCTCCAGCTCCATGATCAC-3'[SEQ ID NO.: 14], and 5'-GTCAGCTTCTTGGAGATGTAGGTCTTGC-3'[SEQ ID NO.: 15]. Gene-specific oligonucleotides used for 3'-directed RACE include 5'-TTGGTTTGGGAGCCTCCTATGTGTGACT-3'[SEQ ID NO.: 16] and 5'-TTGGCGTCTACTGATTCCTCCAACTCTC-3'[SEQ ID NO.: 17]. DNA amplification products were purified with a QIAEX DNA gel extraction kit (Qiagen, Germany) and then cloned into the pT7Blue T-vector (Novagen, Madison, Wis.). For each amplification product, five recombinant clones were isolated and the DNA inserts were sequenced bidirectionally using the Taq DyeDeoxy Terminator Cycle sequencing kit and an ABI Model 373A DNA sequencer (Applied Biosystems, Foster City, Calif.). The entire predicted amino acid sequences of human iPFK-2 and liver PFK-2 were aligned with the Lipman-Pearson method using the DNAstar MegAlign application (Madison, Wis.) (See FIG. 1).

EXAMPLE 2

This example illustrates that LPS induces peripheral blood monocytes to rapidly express iPFK-2 mRNA and protein. PBMCs were isolated by density gradient centrifugation of whole blood through Ficoll (Ficoll-Paque, endotoxin-tested; Pharmacia, Piscataway, N.J.) and then cultured in 6-well plates ($2 \times 10^6$ cells/ml/well RPMI with 10% fetal bovine serum, Hyclone Labs, Logan, Utah). Nonadherent cells were removed by changing the media after 24 hours and the remaining, adherent monocytes were incubated alone as control or in the presence of 1 mg/ml LPS (*E. coli* 0111:B4; Sigma Chemical Co., St. Louis, Mo.). After incubation for 1.5, 3, 6, 12, or 24 hours, cells were lifted, collected by centrifugation at 300 g for 10 min, and immediately analyzed. Total cellular RNA was isolated by a modified guanidinium isothiocyanate method (RNAzol, Cinna Biotecx, Friendswood, Tex.). For RT-PCR analysis, cDNA was prepared from 1.0 mg of total RNA using 0.25 ng of oligo-(dT) and Superscript II following the manufacturer's protocol (Gibco/BRL, Grand Island, N.Y.). Two $\mu$l aliquots of cDNA then were amplified by PCR in a Perkin-Elmer model 9600 thermal cycler using the primers listed below and the following cycling program: denaturation for 15 sec at 95° C., annealing for 20 sec at 55° C., and extension for 30 sec at 72° C. for the indicated cycles with a final extension for 5 min at 72° C. The following human mRNA primers were custom synthesized: β-Actin, 5'-TAAGGAGAAGCTGTGCTACG-3'[SEQ ID NO.: 7], 5'-ATCTCCTTCTGCATCCTGTC-3'[SEQ ID NO.: 8]; IL-1β, 5'-CTGTACCTGTCCTGCGTGTT-3'[SEQ ID NO.: 18], 5'-AGCTCTCTTTAGGAAGACAC-3'[SEQ ID NO.: 19]; iPFK-2, 5'-ATTGGTCTGGCAACTGCAAA-3'[SEQ ID NO.: 9], 5'-GGAGCCTCCTATGTGTGACT-3'[SEQ ID NO.: 10]; Liver PFK-2, 5'-GAAGTCAAA CTGAATGTGTC-3'[SEQ ID NO.: 20], 5'-CCTCTTGTAGGCAGTAAGTC-3'[SEQ ID NO.: 21] (and 5'-AGGCAGTAAGTCTTTATTCG-3'[SEQ ID NO.: 22], 5'-AAGTCAAACTGCCTGTGTCC-3'[SEQ ID NO.: 23], data not shown) (Gibco/BRL). For Northern blot analysis, RNA (7.5 $\mu$g) was electrophoresed through 1.5% agarose-formaldehyde gels, transferred onto nylon membranes (Schleicher & Schuell), and hybridized sequentially with cDNA probes for human iPFK-2 and β-Actin. Probes were produced by PCR using primers described above and then labeled with $^{32}P$ by the random-priming method (Megaprime kit, Amersham). Autoradiography was performed at room temperature for 2–6 hr using DuPont Reflection films and intensifying screens. For Western blot analysis, cells were lysed in 2xLaemle sample buffer for 5 min at 95° C. and total cellular proteins were resolved by electrophoresis through 18% SDS polyacrylamide gels under reducing conditions and transferred onto nitrocellulose membranes (Schleicher & Schuell). Membranes were incubated with rabbit polyclonal anti-human iPFK-2 serum (produced by immunization of rabbits against the following iPFK-2-specific, BSA-conjugated peptide: [NH2]-HRERSRGCKEGT-[COOH], [SEQ ID NO.: 24]. Membranes were then incubated with donkey peroxidase-conjugated anti-rabbit IgG antibody (1:100) and iPFK-2 (approximate molecular mass=50 kD) was visualized by development with luminol (Amersham International, Buckinghamshire, England) (see FIG. 2).

EXAMPLE 3

This example illustrates iPFK-2 mRNA expression by human cancer cell lines. A Northern blot, containing 2 mg of polyA RNA per lane from 8 different human cell lines (Clontech Labs), was hybridized sequentially with cDNA probes for GADPH (Clontech Labs) and iPFK-2 as in example 2 above. The cell lines were: promyelocytic leukemia HL-60, HeLa cell S3, chronic myelogenous leukemia K562, lymphoblastic leukemia MOLT-4, Burkitt's lymphoma Raji, colorectal adenocarcinoma SW480, lung carcinoma A549, and melanoma G361. For RT-PCR analysis, two ml aliquots of K562 cDNA were amplified by PCR for the indicated cycles in a Perkin-Elmer model 9600 thermal cycler using β-Actin-, iPFK-2, or liver PFK-2-specific primers (primer sequences listed in example 2 above). These data (shown in FIG. 3) show that iPFK-2 is expressed by a large variety of human cancer cell lines and is a likely tumor marker enzyme sequence that can be used to measure the progress of cancer treatment and to initially identify cells as cancerous.

EXAMPLE 4

This example illustrates that iPFK-2-specific anti-sense oligonucleotides inhibit K562 cell proliferation in vitro. K562 cells (ATCC) in exponential growth phase were cultured in triplicate in 96-well plates ($5 \times 10^3$ cells/well) in RPMI (Gibco/BRL) supplemented with 10% FBS. Cells were incubated with PBS as control or transfected by the lipofectin method (Gibco/BRL) for 20 hours with the following phosphorothioate oligonucleotides: S-iPFK-2 (A) (sense, position 35–55): 5'-AGCCGCGAAGATGCCGTTGG-3'[SEQ ID NO.: 1]; AS-iPFK-2 (A) (anti-sense, position 35–55): 5'-CCAACGGCATCTTCGCGGCT-3'[SEQ ID NO.: 2]; S-iPFK-2 (B) (sense, position 42–62:

5'-AAGATGCCGTTGGAACTGAC-3'[SEQ ID NO.: 3]; AS-iPFK-2 (B) (anti-sense position 42–62): 5'-GTCAGTTCCAACGGCATCTT-3'[SEQ ID NO.: 4]. Western blot analysis was performed as provided in example 2. Total cellular fructose-2,6-bisphosphate and 5-phosphoribosyl 1-pyrophosphate were measured using the methods described in Van Schaftingen, *Methods. Enz. Anal.* 6:335–341, 1984 and Sant, et al., *J. Biol. Biochem.* 267:16:11038–11045, 1992, respectively. K562 proliferative activity was measured by the incorporation of [$^3$H] thymidine (4 mCi/ml) (DuPont, Boston, Mass.) into DNA over the last 16 hours of incubation/transfection as quantified by liquid scintillation counting. Data in FIG. 4 are expressed as the mean±SD (n=3). Statistical significance was assessed by two sample T-tests (assuming unequal variances) (*, p<0.05) (Taetle, et al., *Cancer Trmt. Reports* 71:297–304, 1987). FIG. 4 shows that a group of antisense oligonucleotides have iPFK-2 antagonist activity and will likely exhibit significant anti-cancer therapeutic activity in view of the widespread prevalence of iPFK-2 and the Warburg effect known for tumor tissue.

EXAMPLE 5

Figure 5:
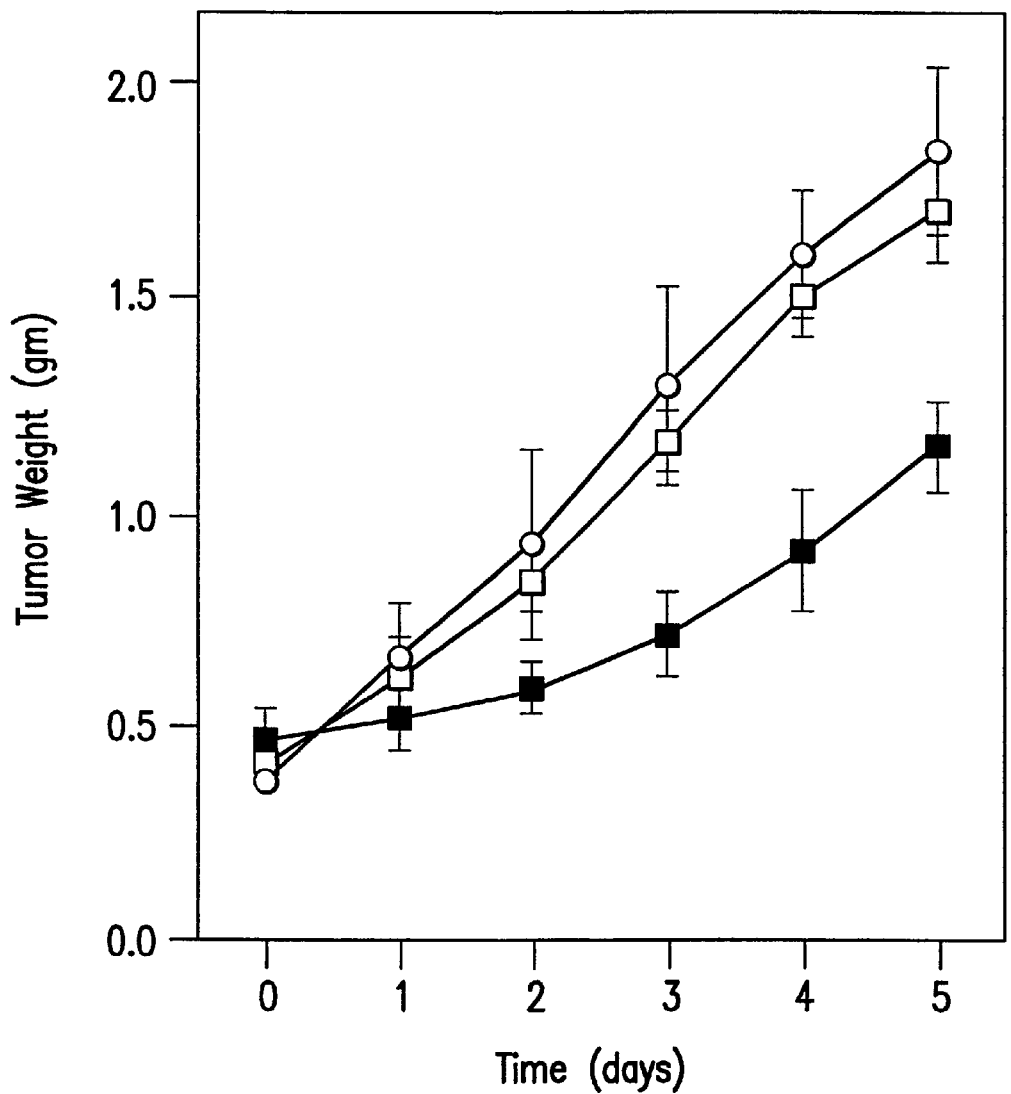
FIG. 5 shows in vivo data providing evidence of iPFK-2 antagonist activity of the antisense oligonucleotides and further showing anti-cancer therapeutic activity of iPFK-2 antagonists.

This example illustrates that iPFK-2-specific anti-sense oligonucleotides inhibit K-562 tumor growth in vivo. K562 tumor-bearing mice were implanted for the indicated days (FIG. 5) with micro-osmotic pumps containing PBS, (open circles); S-iPFK-2 (B), (open squares); or AS-iPFK-2 (B), (closed circles). K562cells were collected from exponential growth phase culture in RPMI medium supplemented with 10% FCS and then washed twice and resuspended in PBS ($1 \times 10^7$ cells/ml). Groups of 5 female BALB/c nude mice (20 gm) (Harlan Labs) were injected s.c. with 0.10 ml of the K562 suspension ($1 \times 10^6$ cells). The tumors were allowed to grow for 7 days to a mean weight of 0.4 gm before treatment was begun. Alzet micro-osmotic pumps (Alza Corporation, Palo Alto, Calif.) loaded with 0.1 ml of PBS or the phosphorothioate oligonucleotides S-iPFK-2 (B) or AS-iPFK-2 (B) (3.0 mM in PBS, see example 4 for sequences) were implanted s.c. into the tumor-bearing mice. Tumor size after 1, 2, 3, and 4 days was determined with Vernier calipers according the following formula: weight (mg)=(width, mm)2×(length, mm)/2(Taetle et al., *Cancer Trmt. Reports* 71:297–304, 1987). FIG. 5 shows that the antisense oligonucleotides that exhibited iPFK-2 antagonist activity also demonstrate anti-cancer therapeutic activity. Therefore, iPFK-2 antagonists are useful for treating cancers.

EXAMPLE 6

This example illustrates that endotoxemia induces mouse iPFK-2 mRNA expression in spleen and muscle. 10 week-old BALB/c mice (19–20 gm) were injected i.p. with LPS (12.5 mg/kg) or saline as control. After 6 and 24 hours mice were euthanized by $CO_2$ asphyxiation and the brain, liver, lower extremity muscles, and spleen were removed by dissection. Total RNA extraction and Northern blot analysis were performed as above using a mouse iPFK-2-specific cDNA probe (amplified from mouse peritoneal macrophage cDNA by 30 cycle RT-PCR using the following human iPFK-2-specific primers: 5'-TGAGGCAGACGTGTCGGTTC-3'[SEQ ID NO.: 25], 5'-CAGCAGCTCCAGGAAAGTGT-3'[SEQ ID NO.: 26]).

Figure 6:
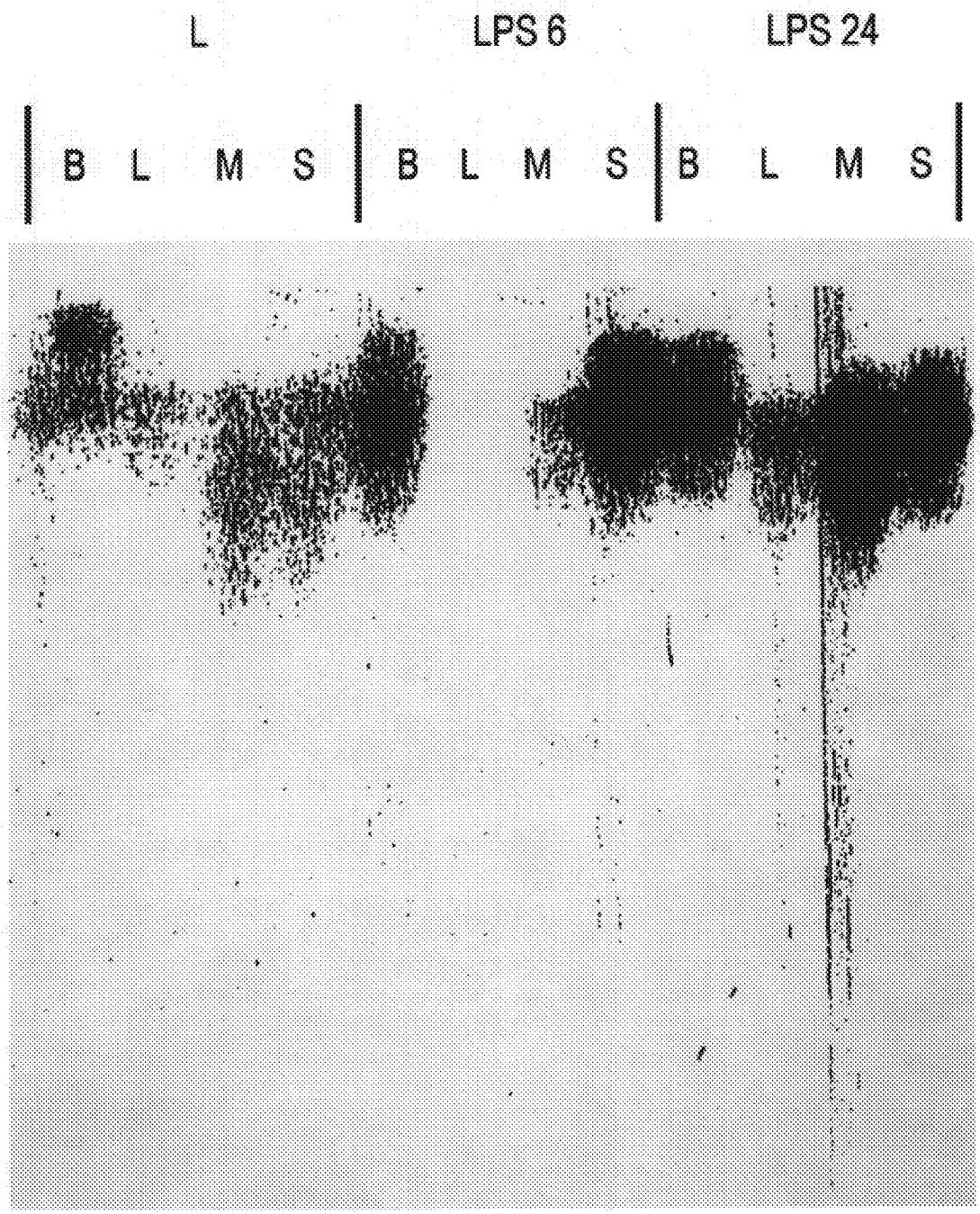
FIG. 6 shows that in vivo endotoxemia induces mouse iPFK-2 mRNA expression in spleen and muscle tissue. 10 week-old BALB/c mice (19–20 gm) were injected i.p. with LPS (12.5 mg/kg) or saline as control. After 6 and 24 hours mice were euthanized by $CO_2$ asphyxiation and the brain, liver, lower extremity muscles, and spleen were removed by dissection. Total RNA extraction and Northern blot analysis were performed using a mouse iPFK-2-specific cDNA probe (amplified from mouse peritoneal macrophage cDNA by 30 cycle RT-PCR using the following human iPFK-2-specific primers: 5'-TGAGGCAGACGTGTCGGTTC-3'[SEQ ID NO.: 5], 5'-CAGCAGCTCCAGGAAAGTGT-3'[SEQ ID NO.: 6]. These in vivo data show that LPS induce iPFK-2 mRNA expression in mice.

The results are presented in FIG. 6 and show that LPS induced iPFK-2 mRNA expression in mice. These data illustrate the predictive pharmacologic importance of iPFK-2 as a therapeutic marker for inflammatory conditions.

EXAMPLE 7

This example illustrates that iPFK-2 is overexpressed in peripheral blood mononuclear cells (PBMCs) of HIV+ individuals. Total RNA was isolated from 3 uninfected individuals (lanes 1–3) and 5 HIV+ individuals (lanes 4–8) and analyzed by RT-PCR with β-Actin-specific primers (5'-TAAGGAGAAGCTGTGCTACG-3'[SEQ ID NO.: 7], 5'-ATCTCCTTCTGCATCCTGTC-3'[SEQ ID NO.: 8], 19 cycles) and iPFK-2-specific primers (5'-ATTGGTCTGGCAACTGCAAA-3'[SEQ ID NO.: 9], 5'-GGAGCCTCCTATGTGTGACT-3'[SEQ ID NO.: 10], 23 cycles).

Figure 7:
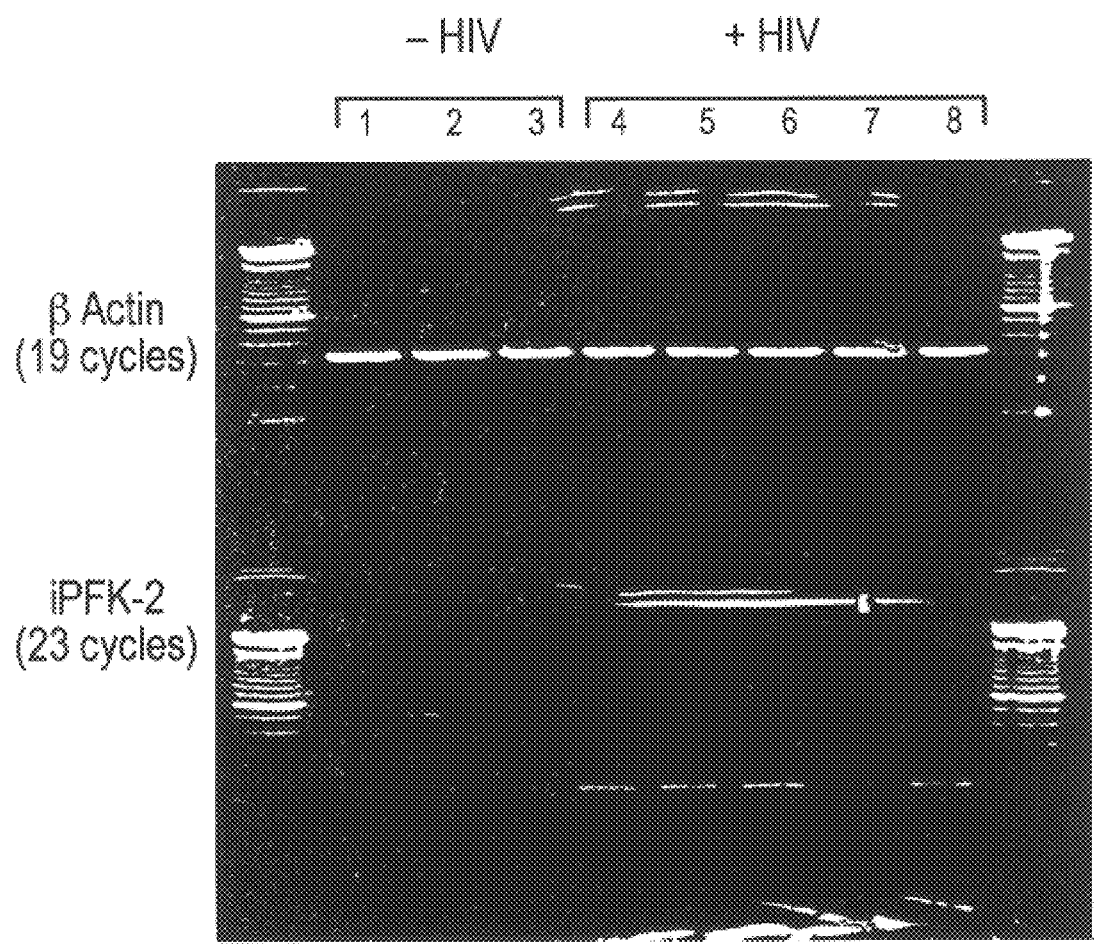
FIG. 7 shows that iPFK-2 is overexpressed in PBMCs (peripheral blood mononuclear cells) of HIV+ individuals. Total RNA was isolated from 3 uninfected individuals (lanes 1–3) and 5 HIV+ individuals (lanes 4–8) and analyzed by RT-PCR with β-Actin-specific primers (5'-TAAGGAGAAGCTGTGCTACG-3'[SEQ ID NO.: 7], 5'-ATCTCCTTCTGCATCCTGTC-3'[SEQ ID NO.: 8], 19 cycles) and iPFK-2-specific primers (5'-ATTGGTCTGGCAACTGCAAA-3'[SEQ ID NO.: 9], 5'-GGAGCCTCCTATGTGTGACT-3'[SEQ ID NO.: 10], 23 cycles).
Figure 8:
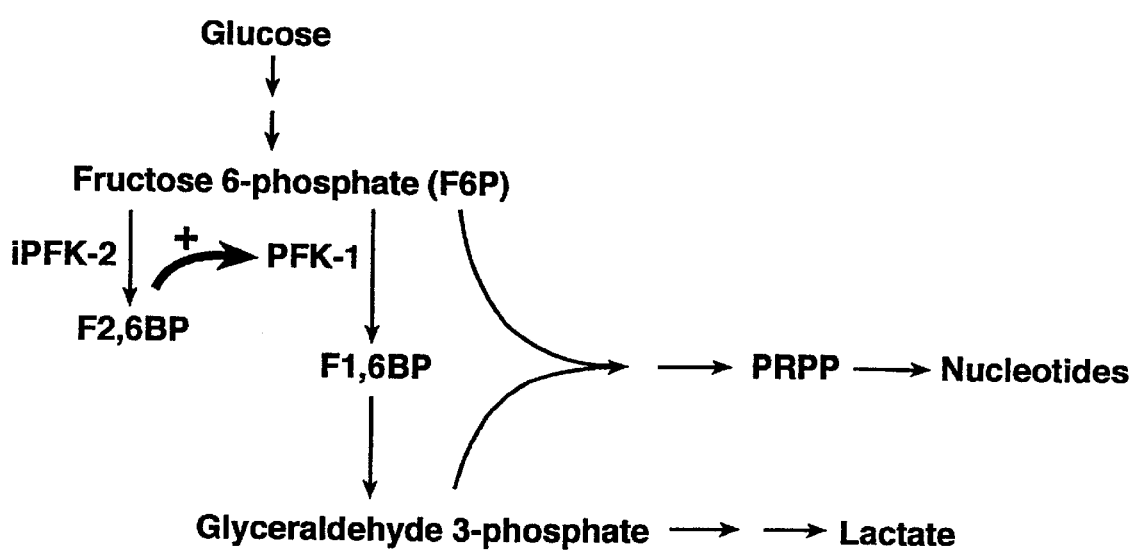
FIG. 8 shows a postulated metabolic scheme for the metabolic role of iPFK-2, particularly in rapidly dividing cancer cells where there is a buildup of lactate from anaerobic metabolism and production of nucleotides to support rapid cell division.

The results are presented in FIG. 7, which shows that iPFK-2 is over-expressed in PBMCs from HIV+ individuals.

EXAMPLE 8

This example illustrates anti-tumor therapeutic activity of iPFK-2 antagonists. The small molecule iPFK-2 antagonist 2,5-anhydro-D-mannitol was found to be an effective inhibitor of iPFK-2 enzymatic activity when using recombinant iPFK-2 polypeptide as provided herein. 2,5-anhydro-D-mannitol was further tested in an in vitro assay of anti-tumor therapeutic activity to try to correlate iPFK-2 inhibition of enzymatic activity with therapeutic anti-tumor pharmacologic activity. K562 tumor cells ($1 \times 10^4$ cells grown in RPMI supplemented with 10% FBS) were exposed to different concentrations of 2,5-anhydro-D-mannitol or to control sugar (glucose) for 12 hours. A cell proliferation assay with tritiated thymidine measured tumor cell proliferation. The data show that 2,5-anhydro-D-mannitol inhibited tumor cell proliferation in a dose-response fashion. 2,5-anhydro-D-mannitol is also able to inhibit iPFK-2 enzymatic activity and can therefore be considered as a iPFK-2 antagonist. These data show an anti-tumor dose response exists for an iPFK-2 antagonist small molecule agent.

Figure 9:
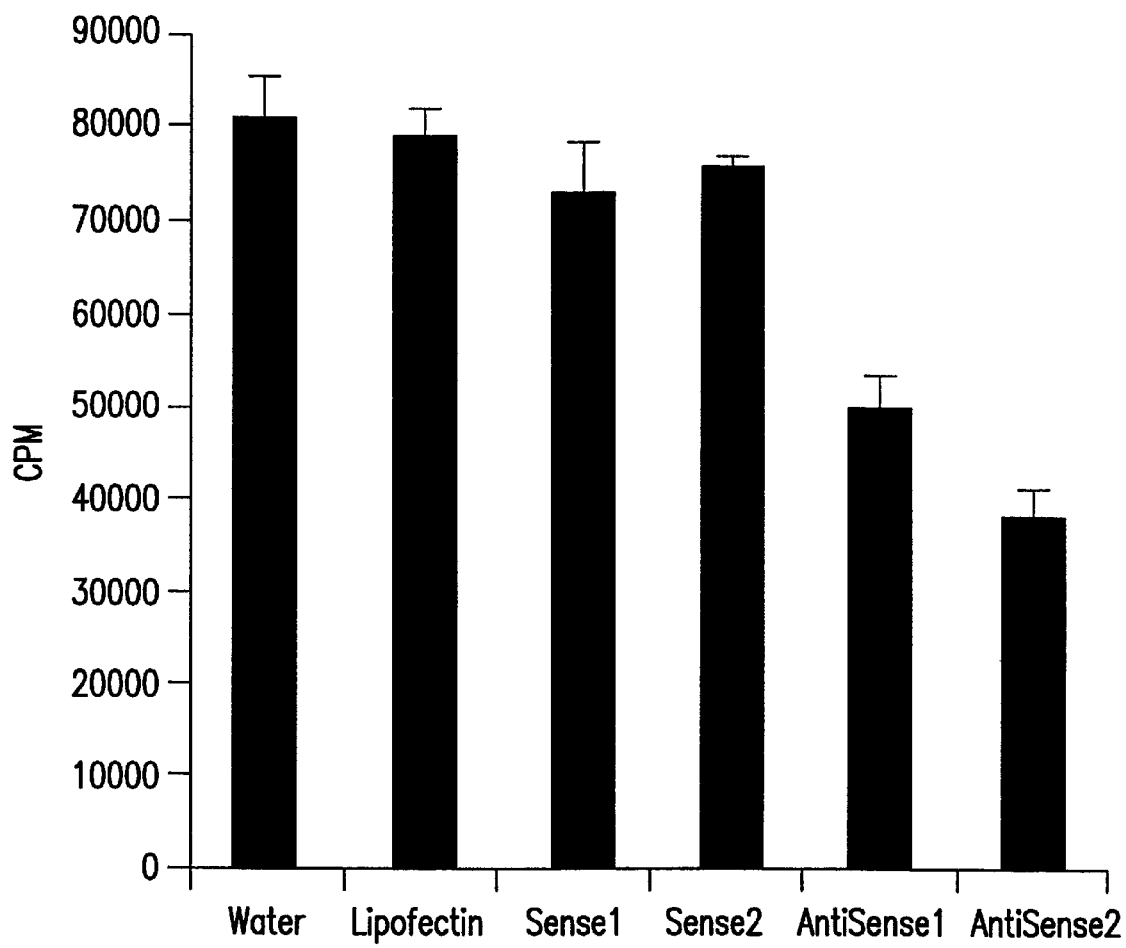
FIG. 9 shows the results of iPFK-2 antisense oligonucleotides inhibiting the proliferation of T cell tumor line MOLT-4. Two different iPFK-2 antisense oligonucleotides were effective and exhibited pharmacologic anti-tumor activity in this predictive assay.

A similar tumor cell proliferation assay was also conducted with two different iPFK-2 antisense oligonuclotides using the T cell tumor cell line MOLT-4. As shown in FIG. 9, both antisense oligonucleotides inhibited tumor cell proliferation and exhibited anti-tumor therapeutic activity in this predictive in vitro assay.

We claim:

1. An anticancer pharmaceutical composition comprising a specific antisense oligonucleotide of at least 10 bases to the iPFK-2 cDNA sequence [SEQ ID NO. 11] and a pharmaceutically acceptable oligonucleotide carrier.

2. The anticancer pharmaceutical composition of claim 1 wherein the antisense oligonucleotide is selected from a 15–50 base oligonucleotide incorporating an oligonucleotide sequence selected from the group consisting of: 5'-CCAACGGCATCTTCGCGGCT-3'[SEQ ID NO: 2], 5'-GTCAGTTCCAACGGCATCTT-3'[SEQ ID NO: 4], and combinations thereof.

3. An anti-inflammatory pharmaceutical composition comprising a specific antisense oligonucleotide of at least 10 bases to the iPFK-2 cDNA sequence [SEQ ID NO. 11] and a pharmaceutically acceptable oligonucleotide carrier.

4. The anti-inflammatory pharmaceutical composition of claim 3 wherein the antisense oligonucleotide is selected from a 15–50 base oligonucleotide incorporating an oligonucleotide sequence selected from the group consisting of: 5'-CCAACGGCATCTTCGCGGCT-3'[SEQ ID NO: 2], 5'-GTCAGTTCCAACGGCATCTT-3'[SEQ ID NO: 4], and combinations thereof.

5. An antisense oligonucleotide of at least 10 bases complementary to the iPFK-2 cDNA sequence [SEQ ID NO. 11].

6. The antisense oligonucleotide of claim 5 wherein the antisense oligonucleotide is selected from a 15–50 base oligonucleotide incorporating an oligonucleotide sequence selected from the group consisting of: 5'-CCAACGGCATCTTCGCGGCT-3'[SEQ ID NO. 2], 5'-GTCAGTTCCAACGGCATCTT-3'[SEQ ID NO. 4], and combinations thereof.

7. A method for treating inflammatory diseases, comprising administering an effective amount of an iPFK-2 antagonist.

8. The method of claim 7 wherein the iPFK-2 antagonist is an enzymatic inhibitor, an anti-iPFK-2 antibody, or a iPFK-2 antisense molecule.

9. A method for treating rapidly-growing cancers, comprising administering an effective amount of an iPFK-2 antagonist.

10. The method of claim 9 wherein the iPFK-2 antagonist is an enzymatic inhibitor, an anti-iPFK-2 antibody, or a iPFK-2 antisense molecule.

* * * * *